(12) United States Patent
Uchida et al.

(10) Patent No.: US 10,571,479 B2
(45) Date of Patent: Feb. 25, 2020

(54) VITAMIN D MEASUREMENT METHOD AND MEASUREMENT KIT

(71) Applicant: FUJIREBIO INC., Shinjuku-ku (JP)

(72) Inventors: Yoshiaki Uchida, Tokyo (JP); Takuya Sakyu, Tokyo (JP); Kazuya Omi, Tokyo (JP)

(73) Assignee: FUJIREBIO INC., Shinjuku-ku (JP)

( * ) Notice: Subject to any disclaimer, the term of this patent is extended or adjusted under 35 U.S.C. 154(b) by 58 days.

(21) Appl. No.: 14/762,263

(22) PCT Filed: Jan. 20, 2014

(86) PCT No.: PCT/JP2014/050996
§ 371 (c)(1),
(2) Date: Jul. 21, 2015

(87) PCT Pub. No.: WO2014/122972
PCT Pub. Date: Aug. 14, 2014

(65) Prior Publication Data
US 2015/0355202 A1    Dec. 10, 2015

(30) Foreign Application Priority Data

Feb. 6, 2013 (JP) .................................. 2013-021284

(51) Int. Cl.
*G01N 33/82* (2006.01)

(52) U.S. Cl.
CPC .... *G01N 33/82* (2013.01); *Y10T 436/203332* (2015.01)

(58) Field of Classification Search
CPC .................................................... G01N 33/82
See application file for complete search history.

(56) References Cited

U.S. PATENT DOCUMENTS

| 7,087,395 | B1 | 8/2006 | Garrity et al. |
| 7,482,162 | B2 | 1/2009 | Laurie et al. |

(Continued)

FOREIGN PATENT DOCUMENTS

| CN | 2049359 U | 12/1989 |
| CN | 102253130 A | 11/2011 |

(Continued)

OTHER PUBLICATIONS

Extended European Search Report dated Aug. 10, 2016 in Patent Application No. 14749104.7.

(Continued)

*Primary Examiner* — Krishnan S Menon
*Assistant Examiner* — Dwan A Gerido
(74) *Attorney, Agent, or Firm* — Oblon, McClelland, Maier & Neustadt, L.L.P.

(57) ABSTRACT

The present invention provides a method of measuring a vitamin D.
Specifically, the present invention provides a method of measuring a vitamin D, comprising:
(1) treating a sample with a surfactant having a steroid skeleton; and
(2) detecting the vitamin D in the treated sample.
The present invention also provides a kit for measuring a vitamin D, comprising:
(1) a surfactant having a steroid skeleton; and
(2) an affinity substance for a vitamin D and/or a vitamin D standard.
Examples of the surfactant having the steroid skeleton may include a bile acid or a derivative thereof or a salt thereof.

11 Claims, 7 Drawing Sheets

(56) References Cited

U.S. PATENT DOCUMENTS

| | | | |
|---|---|---|---|
| 7,534,419 | B2 | 5/2009 | Lewandrowski et al. |
| 7,776,544 | B2 | 8/2010 | Gupta |
| 7,964,363 | B2 | 6/2011 | Armbruster et al. |
| 8,003,400 | B2 | 8/2011 | Kobold et al. |
| 2004/0096900 | A1 | 5/2004 | Laurie et al. |
| 2004/0132104 | A1 | 7/2004 | Sackrison et al. |
| 2005/0084908 | A1 | 4/2005 | Esaki |
| 2009/0093445 | A1 | 4/2009 | Kyriatsoulis et al. |
| 2010/0068725 | A1 | 3/2010 | Armbruster et al. |
| 2010/0285603 | A1 | 11/2010 | Kobold et al. |
| 2011/0195404 | A1* | 8/2011 | Selinfreund ............. C12Q 1/40 435/6.1 |
| 2012/0219966 | A1* | 8/2012 | Kawamura ........ G01N 33/6866 435/7.9 |
| 2014/0113885 | A1* | 4/2014 | Thadhani ............... G01N 33/82 514/167 |
| 2015/0037813 | A1 | 2/2015 | Omi et al. |
| 2015/0104876 | A1 | 4/2015 | Kyriatsoulis et al. |

FOREIGN PATENT DOCUMENTS

| | | |
|---|---|---|
| CN | 102687015 A | 9/2012 |
| EP | 1 352 238 B1 | 6/2006 |
| EP | 1 972 341 A1 | 9/2008 |
| EP | 2 495 565 A1 | 9/2012 |
| JP | 2004 515763 | 5/2004 |
| JP | 2005 503534 | 2/2005 |
| JP | 2005 257271 | 9/2005 |
| JP | 2009 510415 | 3/2009 |
| JP | 2009 540275 | 11/2009 |
| JP | 2010 518369 | 5/2010 |
| KR | 10-2012-0101421 A | 9/2012 |
| WO | 02 46746 | 6/2002 |
| WO | 02 057795 | 7/2002 |
| WO | WO 03/071273 A1 | 8/2003 |
| WO | 03 104820 | 12/2003 |
| WO | 2004 063704 | 7/2004 |
| WO | 2007 039194 | 4/2007 |
| WO | 2007 140962 | 12/2007 |
| WO | 2008 092917 | 8/2008 |
| WO | 2011 052620 | 5/2011 |
| WO | WO 2011/122948 A1 | 10/2011 |
| WO | WO 2012/091569 A1 | 7/2012 |

OTHER PUBLICATIONS

Christopher-John L. Farrell, et al., "State-of-the-Art Vitamin D Assays: A Comparison of Automated Immunoassays with Liquid Chromatography-Tandem Mass Spectrometry Methods", Clinical Chemistry, vol. 58, No. 3, XP055291669, 2012, pp. 531-542.

Office Action dated Aug. 26, 2016 in Australian Patent Application No. 2014215330.

U.S. Appl. No. 14/346,615, filed Aug. 18, 2014, US2015/0037813 A1, Omi, et al.

International Search Report dated Apr. 22, 2014 in PCT/JP2014/050996 Filed Jan. 20, 2014.

Combined Office Action and Search Report dated Jun. 3, 2016 in Russian Patent Application No. 2015132524 (with English language translation and English translation of Categories of Cited Documents).

Combined Office Action and Search Report dated Jul. 12, 2016 in Chinese Patent Application No. 201480007574.X (with English language translation and English translation of Categories of Cited Documents).

Office Action dated Apr. 13, 2017 in Korean Patent Application No. 10-2015-7020646 (with unedited computer generated English translation).

* cited by examiner

VITAMIN D MEASUREMENT METHOD AND MEASUREMENT KIT

TECHNICAL FIELD

The present invention relates to a method of measuring a vitamin D, and the like.

BACKGROUND ART

Vitamin D(s) (hereinafter, simply abbreviated as vitamin D) is known to rigidly bind to a binding protein (DBP: a vitamin D-binding protein, also referred to as a Gc globulin) in blood. Thus, in order to precisely measure an amount of vitamin D by an antigen-antibody method, it is necessary to dissociate vitamin D from DBP (pretreatment). As such a pretreatment, an organic solvent (e.g., ethanol, methanol, DMSO) is used in addition to a denaturating agent (e.g., an acid, a protein denaturating agent, a surfactant, a hydrolytic enzyme) (Patent Literatures 1 to 7).

PRIOR ART LITERATURE

Patent literature

Patent Literature 1: WO03/104820
Patent Literature 2: WO07/039194
Patent Literature 3: WO02/046746
Patent Literature 4: WO04/063704
Patent Literature 5: WO08/092917
Patent Literature 6: WO02/057795
Patent Literature 7: WO07/140962

DISCLOSURE OF INVENTION

Problem to be Solved by the Invention

The present invention provides a method of measuring a vitamin D, and the like.

Means for Solving Problem

As a result of an extensive study, the present inventors have found that a vitamin D can be measured precisely by treating a sample containing vitamin D with a surfactant having a steroid skeleton, and the like, and completed the resent invention.

Accordingly, the present invention is as follows.
[1] A method of measuring a vitamin D, comprising:
(1) treating a sample with a surfactant having a steroid skeleton; and
(2) detecting the vitamin D in the treated sample.
[2] The method of [1], wherein the surfactant is a bile acid or a derivative thereof or a salt thereof.
[3] The method of [1] or [2], wherein the surfactant has a steroid skeleton having no hydroxyl group at position 7.
[4] The method of any of [1] to [3], wherein the surfactant is deoxycholic acid or taurodeoxycholic acid or a salt thereof.
[5] The method of any of [1] to [4], further comprising treating the sample with another denaturating agent that is different from the surfactant.
[6] The method of [5], wherein the another denaturating agent is a surfactant comprising a hydrophobic moiety composed of a hydrocarbon chain and a hydrophilic moiety.
[7] The method of any of [1] to [6], wherein the treatment of the sample is carried out by mixing alone.
[8] The method of any of [1] to [7], comprising:
(1') treating the sample with a reaction solution containing the surfactant having a steroid skeleton and an affinity substance for the vitamin D; and
(2') detecting the vitamin D in the treated sample.
[9] The method of any of [1] to [7], comprising:
(1") treating the sample with a pretreatment solution containing a denaturating agent;
(2") treating the sample treated in (1") above with a diluting solution containing the surfactant having a steroid skeleton; and
(3") detecting the vitamin D in the sample treated in (2") above.
[10] The method of any of [1] to [9], wherein the sample is derived from a human.
[11] The method of any of [1] to [10], wherein the sample is a blood-related sample.
[12] A kit for measuring a vitamin D, comprising:
(1) a surfactant having a steroid skeleton; and
(2) an affinity substance for a vitamin D and/or a vitamin D standard.

Effect of the Invention

The present invention is useful for measuring a vitamin D. According to the present invention, the vitamin D can be measured rapidly and simply.

The kit of the present invention is useful for, for example, practicing the method of the present invention conveniently.

Figure 1:
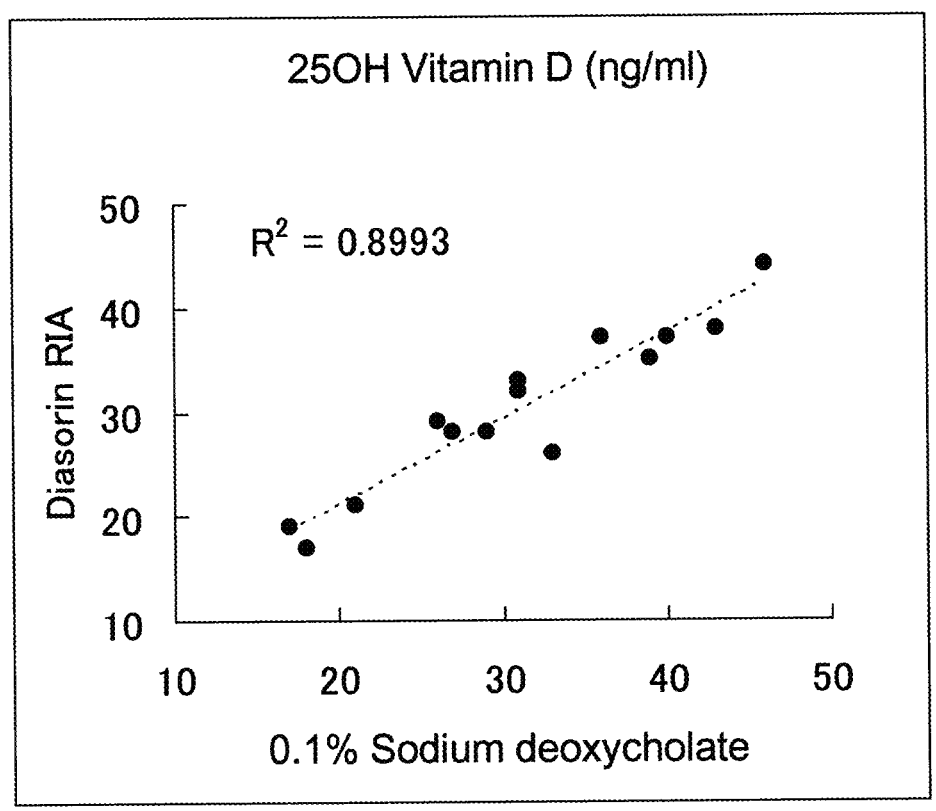
FIG. 1 is a graph illustrating a high correlativity ($R^2=0.8993$) between measured values obtained by treatment of serum samples with sodium deoxycholate and measured values obtained by Diasorin RIA.
Figure 2:
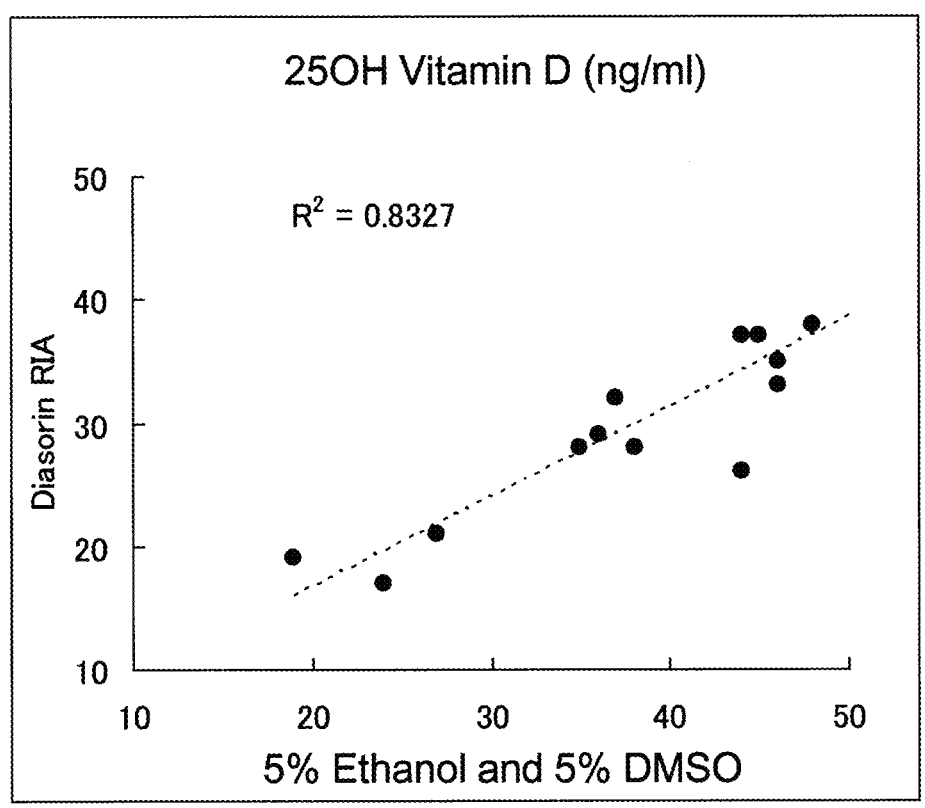
FIG. 2 is graph illustrating a low correlativity ($R^2=0.8327$) between measured values obtained by treatment of serum samples with an organic solvent and measured values obtained by Diasorin RIA.

EMBODIMENT FOR CARRYING OUT THE INVENTION (A. Method of Measuring Vitamin D)

The present invention provides a method of measuring a vitamin D.

The method of the present invention comprises:

(1) treating a sample with a surfactant having a steroid skeleton; and (2) detecting the vitamin D in the treated sample.

(A-1. Step 1)

First, a sample is treated with a surfactant having a steroid skeleton.

The sample used for the method of present invention is a sample containing or suspected of containing a vitamin D or a metabolite thereof as described below. Examples of the metabolite of vitamin D may include 25-OH vitamin D2, 25-OH vitamin D3, 1, 25-(OH)$_2$ vitamin D2 and 1, 25-(OH)$_2$ vitamin D3, which are compounds in which a hydroxyl group(s) is (are) added to the vitamin D. As used herein, unless otherwise indicated, the term "vitamin D" is meant to comprehensively include vitamin D2 and vitamin D3, drugs analogous to the vitamin D2 and vitamin D3, as well as metabolites thereof.

[Chemical 1]

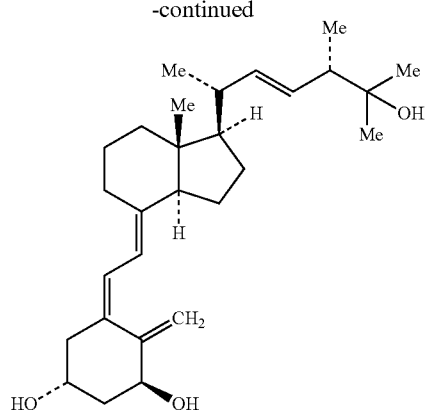

Vitamin D2

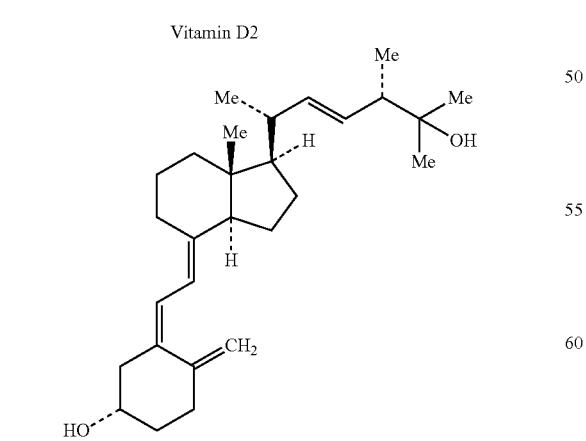

25OH Vitamin D2

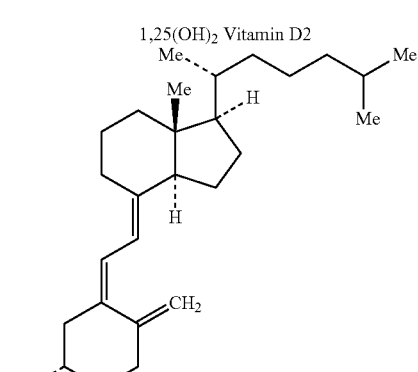

1,25(OH)$_2$ Vitamin D2

Vitamin D3

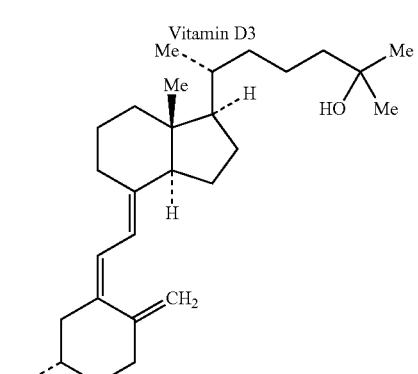

25OH Vitamin D3

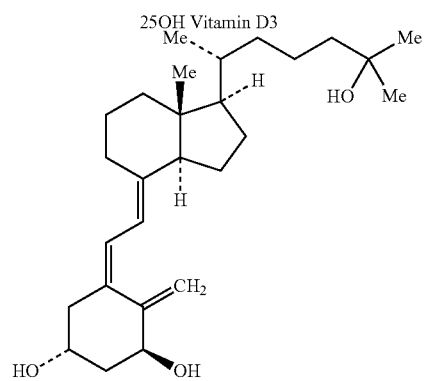

1,25(OH)$_2$ Vitamin D3

An origin of the sample is not particularly limited, and may be a biological sample derived from an organism or an environmental sample or the like. Examples of the organism from which the biological sample is derived may include animals such as mammalian animals (e.g., humans, monkeys, mice, rats, rabbits, cattle, pigs, horses, goats, sheep) and birds (e.g., chickens), insects, microorganisms, plants, bacteria and fishes, and is preferably the mammalian animals, the bacteria and the fishes, more preferably the mammalian animals, and still more preferably the humans. The biological sample may also be a blood sample itself or a blood related sample that is a sample derived from the blood (e.g., whole blood, serum, plasma), saliva, urine, milk, a tissue extract or a cell extract, or a mixture thereof, and the blood related sample is preferred. The environmental sample may include samples derived from soils, sea water and fresh water.

The sample used in the method of the present invention is preferably a sample comprising a complex of vitamin D and a molecule having an ability to bind therewith. The method of the present invention has an advantage that the vitamin D can be measured precisely even when a molecule having a strong binding ability to the vitamin D (protein) is present in the sample. For example, the vitamin D is known to rigidly bind to DBP present in human serum and its dissociation constant has been reported to be $Kd=5\times10^{-8}$ (see Patent Literature 4). However, according to the method of the present invention, the vitamin D in the sample can be measured precisely even when the protein having such a strong binding ability is present in the sample. Therefore, it is thought that according to the method of the present invention, the vitamin D can be measured precisely even if a molecule other than DBP having the ability to bind with the vitamin D (e.g., a molecule potentially having the ability to bind with the vitamin D) is present in the sample. Examples of the other molecule having the ability to bind with the vitamin D may include albumin and lipids. Specifically, examples of the sample comprising the complex of the vitamin D and the molecule having the ability to bind therewith may include the blood related samples (e.g., whole blood, serum, plasma).

According to the method of the present invention, the vitamin D in the sample can be measured irrespective of the presence or absence of a molecule having the ability to bind with the vitamin D in the sample, a type of the molecule and a type of the sample. That is, the method of the present invention can measure the vitamin D in a sample even when an unknown molecule having the ability to bind with the vitamin D is present in the sample, without preliminarily confirming information for these matters. Thus, the method of the present invention can be used as a standard method that may be commonly used for measuring the vitamin D.

In the method of the present invention, a sample may be subjected to other treatment before being treated with a surfactant having a steroid skeleton. Such a treatment may include centrifugation, extraction, filtration, precipitation, heating, freezing, refrigerating, and stirring.

A volume of a sample to be treated with a surfactant having a steroid skeleton is not particularly limited as long as the vitamin D can be measured, and is, for example, 0.1 to 1000 μL, preferably 0.5 to 100 μL and more preferably 1 to 50 μL.

A surfactant having a steroid skeleton is a compound having the steroid skeleton as an independent cyclic structure (i.e., the steroid skeleton not condensed with the other ring) or a salt thereof. A steric structure at position 5 may be in an α form or a β form in the surfactant having the steroid skeleton.

The surfactant having the steroid skeleton may be a compound having the steroid skeleton as a hydrophobic moiety and a hydrophilic moiety, or a salt thereof. Examples of the hydrophilic moiety may include an anionic moiety [e.g., sulfonate ($-SO_3^-$), carboxylate ($-COO^-$) and phosphonate ($-POO_2^-$)], a cationic moiety (e.g., quaternary ammonium and quaternary phosphonium that may be substituted with 1 to 4 hydrocarbon groups), a nonionic hydrophilic moiety (e.g., multiple ethers) and groups having them (e.g., a hydrocarbon group having such a hydrophilic moiety). Thus, the surfactant having the steroid skeleton may be an anionic surfactant, a cationic surfactant, an amphoteric surfactant or a nonionic surfactant depending on a type of the hydrophilic moiety. Examples of the aforementioned hydrocarbon group may include methyl, ethyl, propyl, isopropyl, butyl, iso-butyl, sec-butyl, tert-butyl, pentyl, hexyl, heptyl, octyl, nonyl, decyl, dodecyl (lauryl), tetradecyl (myristyl), hexadecyl (cetyl), heptadecyl, octadecyl (stearyl), cyclopropyl, cyclobutyl, cyclopentyl, cyclohexyl, cycloheptyl, cyclooctyl, cyclononyl, cyclodecyl, phenyl and naphthalenyl. The hydrocarbon group is preferably a hydrocarbon group having 1 to 10 carbon atoms and more preferably an alkyl group having 1 to 6 carbon atoms.

The steroid skeleton may have 1 to 6 substituents (preferably 1, 2, 3 or 4 substituents) in addition to the hydrophilic moiety. Such a substituent is not particularly limited as long as a nature (e.g., hydrophobicity) of the steroid skeleton is not largely impaired, and examples thereof may include a hydrocarbon group having 1 to 10 carbon atoms, a hydroxyl group, a hydroxyl group substituted with a hydrocarbon group having 1 to 10 carbon atoms (e.g., an alkyloxy group), a hydrocarbon group having 1 to 10 carbon atoms-carbonyl-oxy group (e.g., an alkyl-carbonyl-oxy group), an oxo group, a formyl group, a hydrocarbon group having 1 to 10 carbon atoms-oxy-carbonyl group (e.g., an alkyloxy-carbonyl group), a halogen atom (e.g., a fluorine atom, a chlorine atom, a bromine atom, an iodine atom), and cyano.

The term "salt" used herein is any salt, and examples thereof may include an inorganic salt, an organic salt and an intramolecular salt. Examples of the inorganic salt may include a metal salt, a halogenated salt, an acid addition salt and an ammonium salt. Examples of the metal salt may include salts of an alkali metal (e.g., lithium, sodium, potassium) and salts of an alkaline earth metal (e.g., magnesium, calcium). Examples of halogen in the halogenated salt may include fluorine, bromine, chlorine and iodine. Examples of the acid addition salt that is the inorganic salt may include salts with an inorganic acid such as hydrochloric acid, nitric acid and sulfuric acid. Examples of the organic salt may include salts with an organic base such as trimethylamine, triethylamine and pyridine as well as salts with an organic acid such as oxalic acid.

The surfactant having the steroid skeleton is preferably a bile acid or a derivative thereof or a salt thereof. Examples of the bile acid may include deoxycholic acid, chenodeoxycholic acid, ursodeoxycholic acid, hyodeoxycholic acid, cholic acid, glycocholic acid, taurocholic acid, hyocholic acid, 5α-cyprinol, lithocholic acid, taurodeoxycholic acid, and taurocholic acid. Examples of the derivative of the bile acid may include CHAPS, BIGCHAP and deoxy-BIGCHAP.

More preferably, the surfactant having the steroid skeleton may have a steroid skeleton having no hydroxyl group at position 7. Examples of the surfactant having the steroid skeleton having no hydroxyl group at position 7 may include a surfactant having a steroid skeleton having a group other than the hydroxyl group (e.g., the aforementioned substituent excluding the hydroxyl group) at position 7 and a surfactant having a steroid skeleton having no substituent at position 7 (in other words, a carbon atom at position 7 is bound to a hydrogen atom). Particularly preferably, the surfactant having the steroid skeleton having no hydroxyl group at position 7 is the surfactant having the steroid skeleton having no substituent at position 7. Examples of the surfactant having the steroid skeleton having no substituent at position 7 may include deoxycholic acid, taurodeoxycholic acid, lithocholic acid and 5α-cyprinol, as well as salts thereof.

The treatment of the sample may be carried out using one or a plurality of (e.g., two or three) above surfactants. A concentration of the above surfactant is not particularly limited as long as the concentration is effective for measuring the vitamin D. The concentration can appropriately be adjusted, and may be, for example, 0.001% (w/v) to 10% (w/v).

Specifically, the concentration of such a surfactant when a sample is treated with the surfactant having the steroid skeleton is not particularly limited as long as its action is exerted in a mixed solution of a reaction solution and the sample when the sample is treated by a method using the reaction solution as described later, and may be, for example, 0.001% (w/v) to 5% (w/v). In such a case, the concentration of the surfactant having the steroid skeleton may be preferably 0.005% (w/v) or more, more preferably 0.01% (w/v) or more, and still more preferably 0.02% (w/v) or more. The concentration of the surfactant having the steroid skeleton may also be preferably 1% (w/v) or less, more preferably 0.8% (w/v) or less, still more preferably 0.6% (w/v) or less, and particularly preferably 0.5% (w/v) or less. When a plurality of surfactants is used, the concentration of each surfactant is also as described above.

In addition, the concentration of such a surfactant when a sample is treated with the surfactant having the steroid skeleton is not particularly limited as long as its action is exerted in a mixed solution of a pretreatment solution and the sample when the sample is treated by a method using the pretreatment solution as described later, and may be, for example, 0.001% (w/v) to 10% (w/v). In such a case, the concentration of the surfactant having the steroid skeleton may be preferably 0.005% (w/v) or more, more preferably 0.01% (w/v) or more and still more preferably 0.02% (w/v) or more. The concentration of the surfactant having the steroid skeleton may also be preferably 1% (w/v) or less, more preferably 0.8% (w/v) or less, still more preferably 0.6% (w/v) or less and particularly preferably 0.5% (w/v) or less. When a plurality of surfactants is used, the concentration of each surfactant is also as described above.

Furthermore, the concentration of such a surfactant when a sample is treated with the surfactant having the steroid skeleton is not particularly limited as long as its action is exerted in a mixed solution of a pretreatment solution, a diluting solution and the sample when the sample is treated by a method using the pretreatment solution and the diluting solution as described later, and may be, for example, 0.001% (w/v) to 10% (w/v). In such a case, the concentration of the surfactant having the steroid skeleton may be preferably 0.005% (w/v) or more, more preferably 0.01% (w/v) or more and still more preferably 0.02% (w/v) or more. The concentration of the surfactant having the steroid skeleton may also be preferably 1% (w/v) or less, more preferably 0.8% (w/v) or less, still more preferably 0.6% (w/v) or less and particularly preferably 0.5% (w/v) or less. When a plurality of surfactants is used, the concentration of each surfactant is also as described above.

In one embodiment, the treatment of the sample may be carried out in combination with another denaturating agent that is different from the surfactant having the steroid skeleton in addition to the surfactant having the steroid skeleton. Thus, the method of the present invention may further comprise treating the sample with another denaturating agent. The treatment of the sample with the surfactant having the steroid skeleton and the treatment of the sample with another denaturating agent can be carried out simultaneously or separately, and is preferably carried out simultaneously. Examples of such a denaturating agent may include a surfactant (e.g., an anionic surfactant, a cationic surfactant, an amphoteric surfactant or a nonionic surfactant), a chaotropic agent and a reducing agent. One denaturating agent or a plurality of denaturating agents (e.g., two or three) may be used. Such a denaturating agent may be used at a concentration effective for a denaturating effect, and may be used at a concentration effective for an effect other than the denaturating effect with expecting the effect other than the denaturating effect. For example, a concentration of another denaturating agent when a sample is treated with the another denaturating agent may be the same as the aforementioned concentration of the surfactant having the steroid skeleton.

Examples of the anionic surfactant as the another denaturating agent that is different from the surfactant having the steroid skeleton may include hexylsulfuric acid, octylsulfuric acid, decylsulfuric acid, dodecylsulfuric acid, tetradecylsulfuric acid, hexadecylsulfuric acid, dodecylphosphonic acid, dodecylbenzenesulfonic acid, n-lauroylsarcosine and n-dodecanoylsarcosinic acid, and salts thereof (e.g., aforementioned salts such as sodium salts).

Examples of the cationic surfactant as the another denaturating agent that is different from the surfactant having the steroid skeleton may include quaternary ammonium compounds and quaternary phosphonium compounds (e.g., those substituted with 1 to 4 hydrocarbon groups as described above) as well as salts thereof (e.g., halogenated compounds). Specific examples of the cationic surfactant may include cetyldimethylethyl ammonium, hexadecyltrimethyl ammonium, and myristyltrimethyl ammonium, as well as halogenated compounds thereof (e.g., bromide).

Examples of the amphoteric surfactant as the another denaturating agent that is different from the surfactant having the steroid skeleton may include Zwittergent, ASB-14, ASB-14-4, C7Bz0, EMPIGEN BB surfactant, 3-N(N,N-dimethyloctylammonio)propanesulfonic acid, 3-n(N,N-dimethyloctylammonio)propanesulfonic acid, 3-(decyldimethylammonio)propanesulfonate acid, N-dodecyl N,N-dimethyl-3-ammonio-1-propanesulfonic acid, 3-(N,N-dimethylmyristylammonio)propanesulfonic acid, 3-(N,N-dimethylpalmitylammonio)propanesulfonic acid, and 3-(N,N-dimethyoctadecylammonio)propanesulfonic acid as well as salts thereof (e.g., aforementioned salts such as intramolecular salts).

Examples of the nonionic surfactant as the another denaturating agent that is different from the surfactant having the steroid skeleton may include Brij35, Brij56, saponin derived from bark of plants belonging to the genus *Quillaja*, TritonX-405, TritonX-N 101, TritonX-100, TritonX-705-70, TritonX-305, Tween-20, Tween-40, Tween-60, Tween-80, MEGA-8, MEGA-10, and NP40.

Examples of the chaotropic agent as the another denaturating agent that is different from the surfactant having the steroid skeleton may include guanidine, urea and thiosulfuric acid, as well as salts thereof (e.g., aforementioned salts such as acid addition salts such as hydrochloride salts and metal salts such as potassium salts).

Examples of the reducing agent as the another denaturating agent that is different from the surfactant having the steroid skeleton may include dithiothreitol (DTT), dithioerythritol (DTE), 2-mercaptoethylamine (2MEA), 2-mercaptoethanol (2ME), Tris-2-carboxyethylphosphine hydrochloride (TCEP-HCl), L-cysteine, N-acetyl-L-cysteine, and ascorbic acid.

In a preferred embodiment, the another denaturating agent that is different from the surfactant having the steroid skeleton is a surfactant (including a salt) comprising a hydrophobic moiety composed of a hydrocarbon chain and a hydrophilic moiety.

The hydrophobic moiety in the another denaturating agent is composed of a hydrocarbon chain. The hydrocarbon chain is a straight or branched hydrocarbon group typically having 8 to 60 carbon atoms therein. The surfactant comprising the hydrophobic moiety composed of the hydrocarbon chain and the hydrophilic moiety just has to have at least one such a hydrocarbon chain. The hydrocarbon chain preferably has 10 or more carbon atoms. The hydrocarbon chain has preferably 40 or less, more preferably 30 or less and still more preferably 20 or less carbon atoms in terms of easy synthesis or availability. The hydrocarbon chain particularly preferably has 10 or 11 carbon atoms.

The straight hydrocarbon group may include an alkyl group that is a straight saturated hydrocarbon group and a straight unsaturated hydrocarbon group (e.g., alkenyl and alkynyl groups). Examples of the alkyl groups having 8 to 60 carbon atoms may include octyl, nonyl, decyl, undecyl, dodecyl, tridecyl, tetradecyl, pentadecyl, hexadecyl, heptadecyl, octadecyl, nonadecyl and icosyl. Examples of the straight unsaturated hydrocarbon groups having 8 to 60 carbon atoms may include those having 1 to 4 (preferably 1 or 2) unsaturated bonds (double bond or triple bond).

Examples of the branched hydrocarbon groups may include those obtained by substituting a hydrogen atom on the aforementioned straight or branched hydrocarbon group with 1 to 4 (preferably 1 or 2) hydrocarbon groups having 1 to 10 carbon atoms. The hydrocarbon groups having 1 to 10 carbon atoms may include methyl, ethyl, propyl, iso-propyl, butyl, iso-butyl, sec-butyl, tert-butyl, pentyl, hexyl, heptyl, octyl, nonyl, decyl, cyclopropyl, cyclobutyl, cyclopentyl, cyclohexyl, cycloheptyl, cyclooctyl, cyclononyl, cyclodecyl, phenyl and naphthalenyl.

The hydrocarbon chain that composes the hydrophobic moiety is preferably the straight hydrocarbon group and more preferably the straight hydrocarbon group having 10 or 11 carbon atoms.

Examples of the hydrophilic moiety in the another denaturating agent may include an anionic hydrophilic moiety and a cationic hydrophilic moiety. The surfactant comprising the hydrophobic moiety composed of the hydrocarbon chain and the hydrophilic moiety may have one or two or more hydrophilic moieties and may have both the anionic hydrophilic moiety and the cationic hydrophilic moiety. Examples of the anionic hydrophilic moiety may include a sulfonate group ($-SO_3^-$), a carboxylate group ($-COO^-$) and a phosphonate group ($-POO_2^-$). Examples of the cationic hydrophilic moiety may include an ammonium group ($N^+$) and a phosphonium group ($P^+$). The hydrophilic moiety is preferably a sulfonate group ($-SO_3^-$), a carboxylate group ($-COO^-$), an ammonium group ($N^+$) or a phosphonium group ($P^+$), more preferably a sulfonate group ($-SO_3^-$), a carboxylate group ($-COO^-$), or an ammonium group ($N^+$), still more preferably a sulfonate group ($-SO_3^-$) or a carboxylate group ($-COO^-$), and particularly preferably a sulfonate group ($-SO_3^-$).

The surfactant comprising the hydrophobic moiety composed of the hydrocarbon chain and the hydrophilic moiety may comprise the other moiety (e.g., between the hydrophobic moiety and the hydrophilic moiety) in addition to the hydrophobic moiety composed of the hydrocarbon chain and the hydrophilic moiety. Examples of the other moiety may include cyclic groups (e.g., a cycloalkyl group, an aryl group, a heterocyclic group) and acyclic groups (e.g., an amino group, a carbonyl group, a carbonylamino group).

Specifically, examples of the surfactant comprising the hydrophobic moiety composed of the hydrocarbon chain and the hydrophilic moiety may include hexylsulfuric acid, octylsulfuric acid, decylsulfuric acid, dodecylsulfuric acid, tetradecylsulfuric acid, hexadecylsulfuric acid, dodecylphosphonic acid, dodecylbenzenesulfonic acid, N-lauroylsarcosinic acid and dodecanoylsarcosinic acid, as well as salts thereof.

The treatment of the sample may be carried out using one or a plurality of (e.g., 2 or 3) another denaturating agents. A concentration of another denaturating agent is not particularly limited and can appropriately be adjusted as long as the concentration is effective for measuring the vitamin D. For example, when the surfactant comprising the hydrophobic moiety composed of the hydrocarbon chain and the hydrophilic moiety is used as the another denaturating agent, the concentration of such a surfactant may be, for example, 0.001% (w/v) to 10% (w/v).

Specifically, the concentration of the surfactant comprising the hydrophobic moiety composed of the hydrocarbon chain and the hydrophilic moiety when a sample is treated with such a surfactant is not particularly limited as long as its action is exerted in a mixed solution of a reaction solution. When the sample is treated by a method using the reaction solution as described later, the concentration may be, for example, 0.005% (w/v) to 5% (w/v). In such a case, the concentration of the surfactant comprising the hydrophobic moiety composed of the hydrocarbon chain and the hydrophilic moiety may preferably be 0.01% (w/v) or more, more preferably 0.02% (w/v) or more. Also, the concentration of the surfactant comprising the hydrophobic moiety composed of the hydrocarbon chain and the hydrophilic moiety may preferably be 1% (w/v) or less, more preferably 0.8% (w/v) or less, still more preferably 0.6% (w/v) or less and particularly preferably 0.5% (w/v) or less. When a plurality of the surfactants is used, the concentration of each surfactant is also as described above.

The concentration of the surfactant comprising the hydrophobic moiety composed of the hydrocarbon chain and the hydrophilic moiety when a sample is treated with such a surfactant is not particularly limited as long as its action is exerted in a mixed solution of a pretreatment solution. When the sample is treated by a method using the pretreatment solution as described later, the concentration may be, for example, 0.001% (w/v) to 10% (w/v). In such a case, the concentration of the surfactant comprising the hydrophobic moiety composed of the hydrocarbon chain and the hydrophilic moiety may preferably be 0.01% (w/v) or more, more preferably 0.02% (w/v) or more, and still more preferably 0.03% (w/v) or more. Also, the concentration of the surfactant comprising the hydrophobic moiety composed of the hydrocarbon chain and the hydrophilic moiety may preferably be 1% (w/v) or less, more preferably 0.8% (w/v) or less, still more preferably 0.6% (w/v) or less and particularly preferably 0.5% (w/v) or less. When a plurality of the surfactants is used, the concentration of each surfactant is also as described above.

The treatment of the sample may be carried out in the presence of the other component. Examples of such a component may include an affinity substance for vitamin D, albumin (e.g., bovine serum albumin, human serum albumin), gelatin and skim milk.

The affinity substance for the vitamin D refers to a substance having an ability to bind to the vitamin D, and examples thereof may include an antibody and an aptamer against the vitamin D. The antibody may be a polyclonal antibody or a monoclonal antibody. The antibody may also be a fragment of the antibody (e.g., Fab, F(ab')$_2$), or a recombinant antibody (e.g., scFv). The antibody may further be an antibody-like molecule (e.g., affibody, anticalin, DARPins, monobody) made by a molecular biology technique such as a phage display method and/or a protein engineering technique using an existing protein motif.

The treatment of the sample comprises (a) mixing the sample with an aqueous solution (e.g., buffer) containing the component as described above to prepare a mixed solution, and (b) incubating the mixed solution.

Examples of the buffer may include Tris buffer (Tris-HCl buffer, TE buffer, TAE buffer, TBE buffer, Tris buffered saline), phosphate buffer (e.g., phosphate buffered saline), carbonate buffer (e.g., sodium carbonate/bicarbonate buffer), GOOD buffer (e.g., MES, ADA, PIPES, ACES, cholamine hydrochloride, BES, HEPES, acetamide glycine, tricine, glycine amide, bicin). The treatment of the sample can be carried out under a neutral condition, an acidic condition or an alkaline condition, and is preferably carried out under the neutral condition. Thus, a pH value employed in the treatment of the sample is, for example, 4.0 to 9.5, preferably 5.0 to 9.0, preferably 5.5 to 8.5 and more preferably 6.0 to 8.0. The pH value in the treatment of the sample can be adjusted using the buffer, an acidic substance and an alkaline substance.

A temperature in the treatment of the sample (e.g., above steps (a) and (b)) is not particularly limited as long as it is proper for the surfactant having the steroid skeleton exerting its action, and is, for example, 15 to 60° C., preferably 20 to 50° C., and more preferably 20 to 45° C. A time period required for preparing the mixed solution in (a) is typically 30 seconds or less, preferably 20 seconds or less, more preferably 15 seconds or less and still more preferably 10 seconds or less. An incubation time in (b) is, for example, 60 minutes or less, preferably 30 minutes or less and more preferably 10 minutes or less. In terms of shortening of a treatment time for the measurement, the incubation time may be preferably 5 minutes or less, particularly preferably 3 minutes or less, 2 minutes or less, 1 minute or less, 50 seconds or less, 40 seconds or less, 30 seconds or less, 20 seconds or less, 10 seconds or less, or 5 seconds or less. Thus, in terms of shortening of the treatment time for the measurement, the treatment time of the sample (e.g., a total time of (a) and (b) above) may be 3 minutes or less, 2 minutes or less, 1 minute or less, 50 seconds or less, 40 seconds or less, 30 seconds or less, or 15 seconds or less.

The treatment of the sample may be carried out by mixing alone. That the treatment of the sample is carried out by "mixing alone" means that the treatment of the sample is carried out by (a) above and (b) above is not carried out (i.e., the incubation is unnecessary). In terms of rapid and simple measurement, the treatment of the sample may be carried out by mixing alone.

(A-1-1. Use of Reaction Solution)

In a preferred embodiment, the above step (1) can be carried out by treating a sample with a reaction solution comprising a surfactant having a steroid skeleton and an affinity substance for a vitamin D.

The reaction solution comprises the surfactant having the steroid skeleton and the affinity substance for the vitamin D. The reaction solution may also comprise one or a plurality of (2 or 3 or more) other components as described above including another surfactant that is different from the surfactant having the steroid skeleton (the anionic surfactant, the cationic surfactant, the amphoteric surfactant or the nonionic surfactant), the chaotropic agent and the reducing agent as well as the surfactant comprising the hydrophobic moiety composed of the hydrocarbon chain and the hydrophilic moiety.

A concentration of the surfactant having the steroid skeleton in the reaction solution is not particularly limited as long as its action is exerted in the mixed solution of the reaction solution and the sample, and is, for example, a concentration at which the aforementioned concentration in the mixed solution of the reaction solution and the sample can be accomplished (concentration of the surfactant having the steroid skeleton when the sample is treated with the surfactant having the steroid skeleton). Thus, the concentration of the surfactant having the steroid skeleton in the reaction solution can appropriately be determined based on volumes of the sample and the reaction solution so that the aforementioned concentration is accomplished.

The reaction solution comprises the substance as described above in an aqueous solution (e.g., the buffer as described above). The reaction solution can be a neutral solution, an acidic solution, or an alkaline solution, and is preferably the neutral solution. Thus, a pH value of the reaction solution is, for example, 4.0 to 9.5, preferably 5.0 to 9.0, preferably 5.5 to 8.5, and more preferably 6.0 to 8.0.

A volume of the reaction solution can appropriately be determined depending on a volume and a type of the sample as well as a purpose of an assay (e.g., qualitative or quantitative measurement), and is, for example, 0.1 to 100 times, preferably 0.5 to 50 times, and more preferably 1 to 10 times relative to the volume of the sample.

The treatment of the sample with the reaction solution is appropriately carried out in an adequate manner for exerting the action of the component such as the surfactant having the steroid skeleton contained in the reaction solution. For example, the treatment of the sample with the reaction solution can be carried out in the same way as in the treatment of the sample as described above, and may comprise (a1) mixing the reaction solution with the sample to prepare a mixed solution, and (b1) incubating the mixed solution. Conditions for the temperature and the time period in (a1) and (b1) are the same as those described above in (a) and (b) above.

(A-1-2. Use of Pretreatment Solution and Diluting Solution)

In another preferred embodiment, the above step (1) can be carried out by (i) treating a sample with a pretreatment solution comprising a denaturating agent and (ii) treating the sample treated with the pretreatment solution with a diluting solution comprising a surfactant having a steroid skeleton.

(Step i)

The pretreatment solution comprises the denaturating agent. Examples of the denaturating agent may include the surfactant having the steroid skeleton and another surfactant that is different from the surfactant having the steroid skeleton (e.g., an anionic surfactant, a cationic surfactant, an amphoteric surfactant or a nonionic surfactant), a chaotropic agent and a reducing agent. One or a plurality of (e.g., 2 or 3 or more) denaturing agents may be contained in the pretreatment solution. The pretreatment solution may comprise the same types of one or two or more (e.g., 1 to 3) surfactants (e.g., surfactant having the steroid skeleton and another surfactant) as the surfactants contained in the diluting solution. The pretreatment solution may also comprise the other component as described above.

A concentration of the surfactant having the steroid skeleton in the pretreatment solution is not particularly limited as long as its action is exerted in the mixed solution of the pretreatment solution and the sample, and is, for example, a concentration at which the concentration as described above can be accomplished in the mixed solution of the pretreatment solution and the sample (concentration of the surfactant having the steroid skeleton when the sample is treated with the surfactant having the steroid skeleton). Thus, the concentration of the surfactant having the steroid skeleton in the pretreatment solution can appropriately be determined based on the volumes of the sample and the pretreatment solution so that the aforementioned concentration is accomplished.

The pretreatment solution comprises the substance as described above in an aqueous solution (e.g., the buffer as described above). The pretreatment solution can be a neutral solution, an acidic solution, or an alkaline solution, and is preferably the neutral solution. Thus, a pH value of the pretreatment solution is, for example, 4.0 to 9.5, preferably 5.0 to 9.0, preferably 5.5 to 8.5, and more preferably 6.0 to 8.0.

A volume of the pretreatment solution can appropriately be determined depending on a volume and a type of the sample as well as a purpose of an assay (e.g., qualitative or quantitative measurement), and is, for example 0.5 to 100 times, preferably 1 to 10 times, and more preferably 1 to 5 times relative to the volume of the sample.

The treatment of the sample with the pretreatment solution is appropriately carried out in an adequate manner for exerting the action of the component contained in the pretreatment solution. For example, the treatment of the sample with the pretreatment solution can be carried out in the same way as in the treatment of the sample as described above, and may comprise (a2-1) mixing the pretreatment solution with the sample to prepare a first mixed solution, and (b2-1) incubating the first mixed solution. Conditions for the temperature and the time period in (a2-1) and (b2-1) are the same as those described above in (a) and (b) above. The treatment of the sample with the pretreatment solution may be carried out by mixing alone as described above.

(Step ii)

The diluting solution comprises the surfactant having the steroid skeleton. In the method of the present invention, by the use of the diluting solution comprising the surfactant having the steroid skeleton, it is possible to enhance a detection sensitivity for the vitamin D. The diluting solution may also comprise one or a plurality of (e.g., 2 or 3 or more) other components including such as another surfactant that is different from the surfactant having the steroid skeleton (e.g., an anionic surfactant, a cationic surfactant, an amphoteric surfactant or a nonionic surfactant), a chaotropic agent and a reducing agent. The diluting solution may also comprise the other components as described above (e.g., an affinity substance for vitamin D, albumin).

A concentration of the surfactant having the steroid skeleton in the diluting solution is not particularly limited as long as its action is exerted in a mixed solution of the pretreatment solution, the diluting solution and the sample, and is, for example, a concentration at which the concentration as described above can be accomplished in the mixed solution of the pretreatment solution, the diluting solution and the sample (concentration of the surfactant having the steroid skeleton when the sample is treated with the surfactant having the steroid skeleton). Thus, the concentration of the surfactant having the steroid skeleton in the diluting solution can appropriately be determined based on the volumes of the sample, the pretreatment solution, and the diluting solution so that the concentration as described above is accomplished.

The diluting solution comprises the substance as described above in an aqueous solution (e.g., the buffer as described above). The diluting solution can be a neutral solution, an acidic solution, or an alkaline solution, and is preferably the neutral solution. Thus, a pH value of the diluting solution is, for example, 4.0 to 9.5, preferably 5.0 to 9.0, preferably 5.5 to 8.5, and more preferably 6.0 to 8.0.

A volume of the diluting solution can appropriately be determined depending on a volume and a type of the sample as well as a purpose of an assay (e.g., qualitative or quantitative measurement), and can be used in a more volume than a total volume of the sample and the pretreatment solution. Specifically, the volume of the diluting solution is, for example, 1 to 20 times, preferably 1 to 10 times, and more preferably 1 to 5 times relative to the total volume of the sample and the pretreatment solution.

The treatment of the sample with the diluting solution is appropriately carried out in an adequate manner for exerting the action of the surfactant having the steroid skeleton contained in the diluting solution. For example, the treatment of the sample with the diluting solution can be carried out in the same way as in the treatment of the sample with the pretreatment solution, and may comprise (a2-2) mixing the sample treated with the pretreatment solution with the diluting solution to prepare a second mixed solution, and (b2-2) incubating the second mixed solution. Conditions for the temperature and the time period in (a2-2) and (b2-2) are the same as those described above in (a) and (b) above.

(A-2. Step 2)

The vitamin D is detected in the sample treated as described above. The detection of the vitamin D is carried out qualitatively or quantitatively. When the aforementioned affinity substance is used, this step may comprise adding the affinity substance to the treated sample.

The detection of the vitamin D can be carried out by any method, and can be carried out, for example, by utilizing an affinity substance for the vitamin D. The detection of vitamin D may also be carried out by an immunological technique. Examples of such an immunological technique may include an enzyme immunoassay (EIA) (e.g., direct competitive ELISA, indirect competitive ELISA, sandwich ELISA), a radioactive immunoassay (RIA), a fluorescence immunoassay (FIA), a magnetic particle assay, an immunochromatographic method, a luminescence immunoassay, a spin immunoassay, and a latex aggregation method. Examples of a method other than the above methods that enable the detection of the vitamin D may include LC-MS.

When an antibody is used as the affinity substance for vitamin D, a secondary antibody may further be used. The secondary antibody may be an antibody against a primary antibody portion of an antibody (primary antibody) against the vitamin D or an antibody against a complex of the vitamin D and the primary antibody. An antibody such as a secondary antibody may be linked to a substance for detection. Examples of the substance for detection may include enzymes (e.g., horseradish peroxidase, alikaline phosphatase), affinity substances (e.g., streptavidin, biotin), fluorescent substances (e.g., fluorescein, fluorescein isothiocyanate, rhodamine), luminescent substances (e.g., luciferin, aequorin), and radioactive substances (e.g., $^3$H, $^{14}$C, $^{32}$P, $^{35}$S, $^{125}$I). The antibody such as the secondary antibody may be fixed to a support. Examples of the support may include a particle (e.g., a magnetic particle), a membrane (e.g., a nitrocellulose membrane), a glass, a plastic, a metal, a plate (e.g., a multiwell plate), and a device. The antibody may be provided in a form of an antibody immersed in a medium such as a filter paper.

(B. Kit for Measuring Vitamin D)

The present invention also provides a kit for measuring a vitamin D.

The kit of the present invention comprises the followings:
(1) a surfactant having a steroid skeleton; and
(2) an affinity substance for a vitamin D and/or a vitamin D standard.

When the affinity substance for the vitamin D is a primary antibody, the kit of the present invention may further comprise a secondary antibody.

In a preferred embodiment, the kit of the present invention comprises a reaction solution comprising the surfactant having the steroid skeleton and the affinity substance for the vitamin D.

In another preferred embodiment, the kit of the present invention comprises:
(1) a pretreatment solution comprising a denaturating agent;
(2) a diluting solution comprising a surfactant having a steroid skeleton; and
(3) an affinity substance for a vitamin D and/or a vitamin D standard.

Details of the aforementioned constituents comprised in the kit of the present invention (e.g., an effective ingredient and its concentration, and preferred examples) are as described above in the method of the present invention. The reaction solution and the pretreatment solution and the diluting solution may further comprise the components and/or substances described above in the method of the present invention. The vitamin D standard is an aqueous solution comprising (a single or a plurality of) the vitamin D at certain concentration or a vitamin D powder, and is useful as a control.

In the kit of the present invention, each constituent may be provided in a form in which each constituent has been accommodated in each different container (e.g., a tube, a plate). Alternatively, the kit of the present invention may be provided in a form of a device. Specifically, the kit may be provided in a form in which all of the constituents are accommodated in the device. Alternatively, the kit may be provided in a form in which parts of the constituents are accommodated in the device and the remaining are not accommodated in the device (e.g., accommodated in a different container). In this case, the constituent that is not accommodated in the device may be used by injecting it into the device when a target substance is measured. Examples of a device structure may include (1) a device comprising a first section for mixing a surfactant having a steroid skeleton with a sample to prepare a mixed solution and a second section for contacting the prepared mixed solution with an affinity substance for vitamin D to detect the vitamin D; (2) a device comprising a section for mixing the sample, the surfactant having the steroid skeleton and the affinity substance for vitamin D to detect the vitamin D; and (3) a device comprising a flow channel enabling the sample to be mixed with the above constituents (e.g., the reaction solution, and the pretreatment solution and the diluting solution) and a section for detecting the vitamin D.

Hereinafter, Examples of the present invention will be described, but the present invention is not limited thereto.

EXAMPLES

In the following Examples, a primary antibody that recognized 25-OH vitamin D2 and 25-OH vitamin D3 (hereinafter, 25-OH vitamin D2 and 25-OH vitamin D3 are comprehensively abbreviated as 25-OH vitamin D as needed) was used as an immunological technique for measuring a vitamin D. Thus, values measured in the following Examples can correspond to total amounts of 25-OH vitamin D2 and 25-OH vitamin D3.

[Chemical 2]

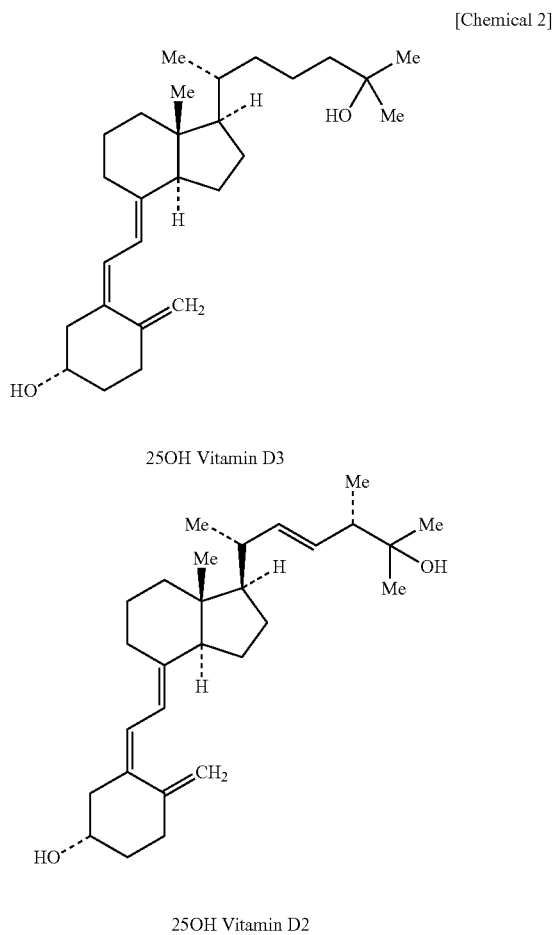

25OH Vitamin D3

25OH Vitamin D2

Example 1

Measurement of 25-OH Vitamin D in Sample Treated with Surfactant

Human serum was treated with a pretreatment solution comprising a surfactant and a diluting solution comprising a surfactant or an organic solvent (ethanol) in combination over time, and then levels of 25-OH vitamin D in the human serum were measured by an immunological method.

The method was carried out as follows.

(1) To the same serum (10 μL) collected from the same person, a pretreatment solution in 4 times its volume (40 μL)

[0.3% (w/v) SDS/0.1 M Tris-HCl buffer (pH 7.6) plus 0.1% (w/v) surfactant described later] was added to prepare a first mixed solution (50 μL) of the serum and the pretreatment solution. A concentration of each component in the first mixed solution is as follows: 0.24% (w/v) SDS/0.1 M Tris-HCl buffer plus 0.08% (w/v) surfactant described later.

(2) The first mixed solution was incubated at room temperature (25° C.) for 10 minutes.

(3) To the incubated first mixed solution, a diluting solution in 3 times its volume (150 μL) [0.1% (w/v) BSA/0.1 M Tris-HCl buffer (pH 7.6), 0.1% (w/v) surfactant described later or 10% (v/v) ethanol] was added to prepare a second mixed solution (200 μL) of the first mixed solution and the diluting solution. A concentration of the surfactant described later in the second mixed solution was 0.095% (w/v).

(4) The second mixed solution was mixed with a solution of anti-25-OH vitamin D antibody-bound magnetic particles in equal volumes.

(5) The solution obtained in (4) above was incubated at 37° C. for 10 minutes.

(6) After the incubation, the magnetic particles in the sample were collected on a magnetic plate, and washed three times.

(7) An alikaline phosphatase-labeled antibody (antibody against an immunocomplex of 25-OH vitamin D and an anti-25-OH vitamin D antibody) solution was added to the magnetic particles after removing the washing solution.

(8) The solution obtained in (7) above was incubated at 37° C. for 10 minutes.

(9) After the incubation, the magnetic particles in the solution were collected on the magnetic plate, and washed three times.

(10) A chromogenic substrate (AMPPD) was added to the solution comprising the magnetic particles.

(11) The solution obtained in (10) above was incubated at 37° C. for 5 minutes.

(12) Luminescence counts were measured using a label reader (ARVO: Perkin Elmer).

Results were as shown in Table 1 below. In Table 1, the luminescence count obtained in the human serum treated with both the pretreatment solution comprising no surfactant and the diluting solution comprising no surfactant was set to 100 (control), and the luminescence counts measured under various condition were expressed as a percent relative to the control.

As a result, a signal intensity (luminescence count) measured using the pretreatment solution comprising CHAPS or sodium deoxycholate (DC Na) that was the surfactant having the steroid skeleton was observed to be prone to be higher than that measured using the surfactant having no steroid skeleton (pretreatment solution) (Table 1). A signal intensity (luminescence count) measured using the diluting solution comprising CHAPS or sodium deoxycholate (DC Na) that was the surfactant having the steroid skeleton was remarkably higher than that measured using the surfactant having no steroid skeleton and the organic solvent (diluting solution) (Table 1). Thus, it was shown that the target substance can be detected with high sensitivity by using the reagent comprising the surfactant having the steroid skeleton and in particular, the target substance can be detected with high sensitivity by using the diluting solution comprising the surfactant having the steroid skeleton.

Example 2

Measurement of 25-OH Vitamin D in Sample Treated with Pretreatment Solution Comprising Chaotropic Agent and Diluting Solution Comprising Surfactant Having Steroid Skeleton in Combination Over Time Human serum was treated with a pretreatment solution comprising a chaotropic agent and a diluting solution comprising a surfactant or an organic solvent (ethanol) in combination over time, and then levels of 25-OH vitamin D in the human serum were measured by the immunological method.

The method was carried out as follows.

(1) To the same serum (10 μL) collected from the same person, a pretreatment solution in 4 times its volume (40 μL) [7.5 M guanidine hydrochloride/PB (phosphate buffer) (pH 7.6) plus 0.1% (w/v) surfactant described later] was added to prepare a first mixed solution (50 μL) of the serum and the pretreatment solution. A concentration of each component in the first mixed solution is as follows: 6 M guanidine hydrochloride; 0.08% (w/v) surfactant described later.

(2) The first mixed solution was incubated at room temperature (25° C.) for 10 minutes.

(3) To the incubated first mixed solution, a diluting solution in 3 times its volume (150 μL) [0.1% (w/v) BSA/0.1 M Tris-HCl buffer (pH 7.6), 0.1% (w/v) surfactant described later or 10% (v/v) ethanol] was added to prepare a second mixed solution (200 μL) of the first mixed solution and the diluting solution. A concentration of the surfactant described later in the second mixed solution was 0.095% (w/v).

TABLE 1

Comparison of luminescence counts in measurement of 25-OH vitamin D level in human serum treated with pretreatment solution comprising surfactant and diluting solution comprising surfactant or organic solvent (ethanol) in combination over time.

| | | Surfactant or organic solvent in diluting solution | | | | | | |
|---|---|---|---|---|---|---|---|---|
| | | NP40 | Tween20 | Saponin | CHAPS | DC Na | None | 10% Ethanol |
| Various surfactant in pretreatment solution | NP40 | 103 | 75 | 110 | 211 | 256 | 111 | 162 |
| | Tween20 | 102 | 70 | 94 | 194 | 217 | 96 | |
| | CHAPS | 125 | 91 | 137 | 270 | 323 | 132 | |
| | DC Na | 120 | 84 | 119 | 262 | 285 | 121 | |
| | None | 110 | 80 | 102 | 249 | 248 | 100 | |

NP40: nonyl phenoxypolyethoxylethanol
Tween 20: polyoxyethylen(20)sorbitan monolaurate
Saponin: saponin derived from bark of plants belonging to the genus *Quillaja* (SIGMA S7900)
CHAPS: 3-(3-cholamidepropyl)dimethylammonio-1-propanesulfonate
DC Na: deoxycholate sodium (4) The subsequent procedures were the same as those in (4) to (12) in Example 1.

Results were as shown in Table 2 below. In Table 2, the luminescence count in the human serum treated with both the pretreatment solution comprising the chaotropic agent (guanidine hydrochloride) and no surfactant and the diluting solution comprising no surfactant was set to 100 (control), and the luminescence counts measured under various condition were expressed as a percent relative to the control.

TABLE 2

Comparison of luminescence counts in measurement of 25-OH vitamin D in human serum treated with pretreatment solution comprising chaotropic agent and diluting solution comprising surfactant or organic solvent in combination over time

| | | Surfactant in diluting solution | | | |
|---|---|---|---|---|---|
| | | Tween20 | DC Na | None | 10% ethanol |
| Major components in pretreatment solution guanidine hydrochloride + each surfactant | Tween 20 | 102 | 197 | 65 | 139 |
| | Dc Na | 130 | 219 | 128 | |
| | None | 130 | 215 | 100 | |

The abbreviations are the same as in Table 1.

As shown in Table 2, the signal intensity measured using the diluting solution comprising sodium deoxycholate even when the serum was treated with the pretreatment solution comprising the chaotropic agent was higher than that measured using the diluting solution comprising the organic solvent or the other surfactant (Tween 20). Thus, it has been confirmed that the method of the present invention can detect the target substance with high sensitivity without being particularly limited by the type of the pretreatment solution.

Example 3

Comparison of Correlation Coefficients Between Measured Values of Target Substance Obtained by Method of the Present Invention Using Pretreatment Solution and Diluting Solution in Combination and Measured Values Obtained by Existing Method In order to verify measurement accuracy of the target substance by the method of the present invention, correlation coefficients between measured values of the target substance obtained by the method of the present invention using the pretreatment solution and the diluting solution in combination and measured values obtained by an existing method utilizing a different methodology were compared.

(3-1) Measurement by Method of the Present Invention

The method was carried out as follows. Total 15 samples of 14 human serum samples plus one sample of enhanced serum treated with charcoal were used as samples for the measurement.

(1) To serum (10 µL), a pretreatment solution in 4 times its volume (40 µL) [7.5 M guanidine hydrochloride and 4 mM DTT/0.1 M Tris buffer (pH 7.6) plus 0.1% (w/v) sodium deoxycholate or 5% (v/v) ethanol and 5% DMSO] was added to prepare a first mixed solution (50 µL).

(2) The first mixed solution was incubated at room temperature (25° C.) for 10 minutes.

(3) To the incubated first mixed solution, a diluting solution in 3 times its volume (150 µL) [0.1% (w/v) BSA/0.1 M phosphate buffer (pH 7.6) plus 0.1% (w/v) sodium deoxycholate or 5% (v/v) ethanol and 0.5% (v/v) DMSO] was added to prepare a second mixed solution of the first mixed solution and the diluting solution.

(4) The subsequent procedures were the same as those in (4) to (12) in Example 1.

(3-2) Measurement by Existing Method

As the existing method utilizing a different methodology, DiaSorin-RIA using a radioactive substance was used as described later. DiaSorin-RIA was carried out using a commercially available kit (25-hydroxy vitamin D $^{125}$I RIA kit supplied from DiaSorin).

Specifically, DiaSorin-RIA was carried out by (I) and (II) described later. As the sample for the measurement, total 15 samples of 14 human serum samples plus one sample of enhanced serum treated with charcoal were used just like (3-1) above.

(I) Pretreatment Procedure (a) Prepare glass test tubes (b) Dispense 500 µL of acetonitrile in each test tube.

(c) Add each 50 µL of a calibrator, a control, or a sample (serum or the like) in each test tube.

(d) Stir the sample solution for 10 seconds.

(e) Centrifuge the sample solution at 1200×g for 10 minutes at room temperature.

(f) Use a supernatant as the sample.

(II) Measurement Procedure (a) Mix 25 µL of the above sample, 50 µL of $^{125}$I 25-OH vitamin D and 1 mL of anti-25-OH vitamin D solution.

(a) Incubate the mixed solution at room temperature for 90 minutes.

(b) Add 500 µL of a donkey-derived anti-goat antibody to the incubated mixed solution.

(c) Incubate the resulting solution at room temperature for 25 minutes.

(d) Add 500 µL of NSB/addition buffer to the incubated solution.

(e) Centrifuge the resulting solution at 1800×g for 20 minutes at room temperature.

(f) Completely remove a supernatant from the centrifuged solution.

(g) Carry out the measurement using a gamma scintillation counter.

(3-3) Results

The measured values obtained by the method of the present invention using the diluting solution comprising sodium deoxycholate had a high correlativity with the measured values obtained by the DiaSorin-RIA method (FIG. 1, $R^2$=0.8993). On the other hand, the measured values obtained using the diluting solution comprising ethanol and DMSO had a low correlativity with the measured values obtained by the DiaSorin-RIA method (FIG. 1, $R^2$=0.8327). Thus, the method of the present invention is thought to be useful for the measurement of vitamin D.

Example 4

Examination of Treatment Time with Surfactant

A treatment time of the treatment with the surfactant, which is required for the measurement of 25-OH vitamin D with high sensitivity was examined.

The method was carried out as follows.

(1) To 10 µL of the same serum obtained from the same person, 40 µL of a pretreatment solution [Tris-HCl buffer (pH 7.6) plus 1% (w/v) sodium deoxycholate] was added to prepare a first mixed solution (50 µL) of the serum and the pretreatment solution by mixing with stirring. The concentration of each component in the first mixed solution is as follows: 0.8% (w/v) sodium deoxycholate. A time required for mixing with stirring was about 3 seconds.

(2) The first mixed solution was incubated at room temperature (25° C.) (for 10 minutes, 5 minutes or one minute). The first mixed solution prepared by mixing with stirring alone was subjected to next procedure without incubating (incubation time: 0 minute).

(3) To the solution obtained in (2) above, 150 μL of a diluting solution [PBS (pH 7.6) plus 0.1% (w/v) sodium deoxycholate and 0.1% (w/v) BSA] was added to prepare a second solution (200 μL) of the first mixed solution and the diluting solution. The concentration of sodium deoxycholate in the second mixed solution was 0.28% (w/v).

(4) The subsequent procedures were the same as those in (4) to (12) in Example 1.

Results were as shown in Table 3 below. In Table 3, the luminescence count measured under the condition of the incubation time for 10 minutes for the treatment with the pretreatment solution containing 0.14% (w/v) sodium deoxycholate was set to 100 (control), and the luminescence counts measured under the condition of the incubation time for 0 minute, 1 minute and 5 minutes were expressed as a ratio relative to the control.

TABLE 3

Relationship between incubation time and relative luminescence count in the presence of surfactant

|  | 10 min | 5 min | 1 min | Mixing alone |
|---|---|---|---|---|
| Na deoxycholate (0.14%) | 100 | 106 | 102 | 101 |

As a result, even in the case of mixing alone (incubation time: 0 minute), the relative luminescence count at nearly comparable level to that in the case of incubating for 10 minutes was obtained. This indicates that the incubation in the above step (1) is not necessarily required and 25-OH vitamin D is dissociated from DBP in the serum by only mixing the serum with the pretreatment solution. Thus, it has been shown that the method of the present invention can shorten the time required for the measurement of the target substance.

Reference Example 1

Time Required for Pretreatment Using Existing Product

The time required for pretreatment of the serum sample using the existing product is described later according to its manufacturer's instructions. DiaSorin-RIA (supplied from DiaSorin) and DiaSorin-Liaison (supplied from DiaSorin) were used as the existing products.

TABLE 4

Time required for pretreatment of existing product

|  | DiaSorin-RIA | DiaSorin-Liaison |
|---|---|---|
| Treatment time (min) | about 10 | about 10 |

DiaSorin-RIA: Protocols attached with kit
DiaSorin-Liaison: 510(K) Number K071480

Example 5

Measurement of Vitamin D Using Surfactant Having Steroid Skeleton, and Anionic, Cationic, or Amphoteric Surfactant The serum was treated with a reaction solution comprising the surfactant having the steroid skeleton (sodium deoxycholate) and an antibody against vitamin D, and then the level of 25-OH vitamin D in the serum was measured by the immunological method. Also, a combination effect of the surfactant having the steroid skeleton and the other surfactant was examined.

Specifically, the method was carried out as follows.

(1) To 3.75 μL of 100 ng/mL enhanced horse serum, 146.25 μL of a reaction solution [Tris-HCl buffer (pH 7.6), 0.03% (w/v) or 0.1% (w/v) surfactant described later, 0.04% (w/v) sodium deoxycholate, 0.04% (w/v) BSA, anti-25-OH vitamin D antibody-bound particle solution] was added to prepare a mixed solution (150 μL) of the serum and the reaction solution. The concentration of each component in the mixed solution is as follows: about 0.03% (w/v) or about 0.1% (w/v) surfactant described later; about 0.04% (w/v) sodium deoxycholate; about 0.04% (w/v) BSA.

(2) The mixed solution was incubated at 37° C. for 10 minutes.

(3) After the incubation, the magnetic particles in the sample were collected on a magnetic plate, and the magnetic particles were washed three times.

(4) An alikaline phosphatase-labeled antibody (antibody against a complex of 25-OH vitamin D and an anti-25-OH vitamin D antibody) suspended in MES buffer was added to the magnetic particles after removing the washing solution.

(5) The solution obtained in (4) above was incubated at 37° C. for 10 minutes.

(6) After the incubation, the magnetic particles in the sample were collected on the magnetic plate, and the magnetic particles were washed three times.

(7) A luminescence substrate (AMPPD) solution was added to the magnetic particles after removing the washing solution.

(8) The solution comprising the magnetic particles and the luminescence substrate was incubated at 37° C. for 5 minutes.

(9) A luminescence count was measured using the label reader (ARVO: Perkin Elmer).

Results were as shown in Table 5 below. In Table 5, the luminescence count in the serum measured under the condition where the aforementioned surfactant [0.03% (w/v) or 0.1% (w/v)] was not added was set to 100 (control), and the luminescence count in the serum measured under the condition where the surfactant having the steroid skeleton was added was expressed as a ratio relative to the control.

TABLE 5

Effect of treatment of sample with surfactant having steroid skeleton on measurement of vitamin D

|  | Anionic | | | | | Cationic | Amphoteric | |
|---|---|---|---|---|---|---|---|---|
|  | (a) | (b) | (c) | (d) | (e) | (f) | (g) | (h) |
| 0.03% | 635 | 91 | 5931 | 1327 | 934 | 773 | 102 | 219 |
| 0.10% | 12496 | 286 | 1721 | 8548 | 6215 | 2021 | 198 | 334 |

The reaction solution comprises 0.03% (w/v) or 0.1% (w/v) surfactant:
(a) sodium deoxycholate,
(b) sodium cholate,
(c) SDS,
(d) N-lauroylsarcosine,
(e) n-dodecanoylsarcosinic acid,
(f) cetyldimethylethyl ammonium bromide,
(g) CHAPS or
(h) Zwittergent, in addition to 0.04% (w/v) sodium deoxycholate (surfactant having the steroid skeleton).

As a result, all of the anionic surfactant, the cationic surfactant and amphoteric surfactant were observed to be prone to enhance the luminescence count in combination with the surfactant having the steroid skeleton (sodium deoxycholate). Sodium deoxycholate, SDS, N-lauroylsarcosine and dodecanoylsarcosinic acid that were the anionic surfactants as well as cetyldimethylethyl ammonium bromide that was the cationic surfactant enhanced the luminescence count. In particular, sodium deoxycholate exhibited remarkable enhancement of the luminescence count.

In addition, in the sample treated with the reaction solution comprising both the surfactant having the steroid skeleton (sodium deoxycholate) and the antibody against vitamin D, we succeeded in measuring the vitamin D level (see the above step (1)). This indicates that even though the surfactant having the steroid skeleton can dissociate the vitamin D from the vitamin D-binding protein contained in the serum, it cannot inhibit the detection of the vitamin D by the antibody. Therefore, according to the present invention, it was shown that the vitamin D could be measured simply using the reaction solution comprising both the surfactant having the steroid skeleton and the antibody against the vitamin D, without utilizing a complicated technique in which the sample is treated separately with the surfactant having the steroid skeleton and with the antibody against the vitamin D.

Example 6

Examination of Effect of Treatment of Sample with Surfactant Having or Not Having Hydroxyl Group at Position 7 in Steroid Skeleton on Measurement of Vitamin D In Example 5, it was confirmed that sodium deoxycholate enhanced the signal intensity more remarkably than sodium cholate and CHAPS (Table 5). Here, sodium deoxycholate is the surfactant that has no hydroxyl group at position 7 in the steroid skeleton, whereas sodium cholate and CHAPS are the surfactants having the hydroxyl group at position 7 in the steroid skeleton. This suggested that the presence or absence of the hydroxyl group at position 7 in the steroid skeleton likely has an effect on the signal intensity. Thus, the effect of the treatment of the sample with the surfactant having or not having the hydroxyl group at position 7 in the steroid skeleton on the measurement of vitamin D was examined.

Specifically, the method was carried out as follows.

(1) To 3.75 μL of 100 ng/mL enhanced horse serum, 146.25 μL of a reaction solution [Tris-HCl buffer (pH 7.6), 0% (w/v), 0.1% (w/v), 0.2% (w/v) or 0.4% (w/v) surfactant having the steroid skeleton described later, 0.04% (w/v) BSA, anti-25-OH vitamin D antibody-bound particle solution] was added to prepare a mixed solution (150 μL) of the serum and the reaction solution. The concentration of each component in the mixed solution is as follows: 0% (w/v), about 0.1% (w/v), about 0.2% (w/v) or about 0.4% (w/v) surfactant having the steroid skeleton described later; about 0.04% (w/v) BSA. Sodium deoxycholate and sodium taurodeoxycholate were used as the surfactant having no hydroxyl group at position 7 in the steroid skeleton, whereas sodium taurocholate, sodium cholate and CHAPS were used as the surfactant having the hydroxyl group at position 7 in the steroid skeleton.

(2) The subsequent steps were carried out in the same manner as those in steps (2) to (9) in Example 5.

Results were as shown in Table 6 below. In Table 6, the luminescence count in the serum measured under the condition where the aforementioned surfactant [0.1% (w/v), 0.2% (w/v) or 0.4% (w/v)] was not added was set to 100 (control), and the luminescence count in the serum measured under the condition where the surfactant having the hydroxyl group at position 7 in the steroid skeleton or the surfactant having no hydroxyl group at position 7 in the steroid skeleton was added was expressed as a ratio relative to the control.

TABLE 6

Effect of the presence or absence of hydroxyl group at position 7 in the steroid skeleton on measurement of vitamin D

| | Hydroxyl group at position 7 in steroid skeleton | | | | |
|---|---|---|---|---|---|
| | Presence | | | Absence | |
| Conc* | Na taurocholate | Na cholate | CHAPS | Na taurodeoxycholate | Na deoxycholate |
| 0.1% | 196 | 154 | 120 | 2411 | 6759 |
| 0.2% | 358 | 461 | 215 | 5194 | 7449 |
| 0.4% | 3937 | 4956 | 1680 | 5483 | 5422 |

Conc*: concentration

As a result, the signal intensity measured in the sample treated with sodium deoxycholate or sodium taurodeoxycholate that had no hydroxyl group at position 7 in the steroid skeleton was remarkably enhanced compared with the signal intensity measured in the sample treated with sodium cholate or sodium taurocholate that had the hydroxyl group at position 7 in the steroid skeleton. Therefore, this Example and Example 1 have shown that the surfactant having the steroid skeleton is effective for the measurement of vitamin D and that the surfactant having no hydroxyl group at position 7 in the steroid skeleton is particularly useful for the measurement of the vitamin D.

Example 7

Measurement of Vitamin D Using Reaction Solution Comprising Surfactant Having Steroid Skeleton, SDS and Antibody A level of 25-OH vitamin D in a human serum sample was measured using a reaction solution comprising the surfactant having the steroid skeleton and SDS for the measurement of vitamin D.

Specifically, the method was carried out as follows.

(1) To 3.75 μL of human sera (#1 to 16) having a different source or human serum treated with charcoal (control 1), 146.25 μL of a reaction solution [Tris-HCl buffer (pH 7.6), 0.14% (w/v) sodium deoxycholate, 0.015% (w/v) SDS, 0.04% (w/v) BSA and anti-25-OH vitamin D antibody-bound particle solution] was added to prepare a mixed solution of the serum and the reaction solution.

(2) The subsequent steps were carried out in the same manner as those in (2) to (9) in Example 5. Measured values obtained were compared with measured values obtained by the DiaSorin-RIA method. The DiaSorin-RIA method was carried out by the method described in Example 3-2.

Figure 3:
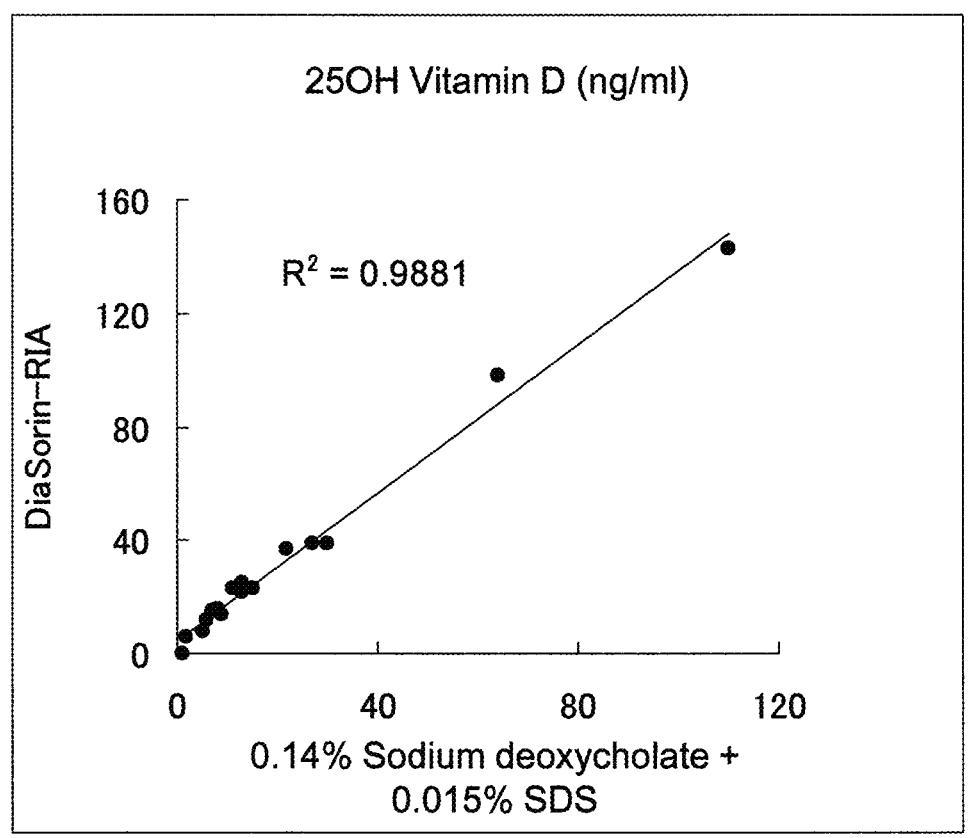
FIG. 3 is a graph illustrating a high correlativity ($R^2=0.9881$) between measured values obtained by treatment of serum samples with a reaction solution containing sodium deoxycholate, SDS and an antibody and measured values obtained by Diasorin RIA.

Results were as shown in Table 7 and FIG. 3. In Table 7, the luminescence count obtained from the human serum treated with charcoal was set to 100 (control), and the luminescence count in the serum measured was expressed as a ratio relative to the control.

TABLE 7

Luminescence count values in the measurement of vitamin D using surfactant having steroid skeleton and SDS

| Human serum sample | 0.14% Na deoxycholate + 0.015% DSD |
|---|---|
| #1 | 145 |
| #2 | 1558 |
| #3 | 1388 |
| #4 | 753 |
| #5 | 1169 |
| #6 | 1541 |
| #7 | 475 |
| #8 | 3586 |
| #9 | 1764 |
| #10 | 610 |
| #11 | 4909 |
| #12 | 371 |
| #13 | 758 |
| #14 | 5974 |
| #15 | 18455 |
| #16 | 31063 |
| Serum treated with charcoal | 100 |

As a result, the measured values obtained by the method of the present invention using the reaction solution comprising the surfactant having the steroid skeleton and SDS had a high correlativity with the measured values obtained by the DiaSorin-RIA method (FIG. 3, $R^2=0.9881$). Therefore, the present invention is thought to be useful for the measurement of vitamin D.

Example 8

Measurement of 25-OH Vitamin D Released From Vitamin D-Binding Protein and Human Serum by Treatment With Surfactant Having Steroid Skeleton (8-1) Treatment of Fraction With Surfactant Having Steroid Skeleton A fraction (control fraction) obtained by eluting human serum treated with control buffer (Tris-HCl) by gel filtration chromatography was subjected to the measurement by an anti-25-OH vitamin D antibody. In addition, the control fraction was treated with sodium deoxycholate, and subjected to the measurement by the anti-25-OH vitamin D antibody.

Specifically, the method was carried out as follows.

(1) To human serum (50 µL), 0.1 M Tris-HCl buffer (pH 7.8) in 4 times its volume (200 µL) was added to prepare a mixed solution. The mixed solution was prepared by mixing alone with stirring (for about 3 seconds) (i.e., without incubation).

(2) Molecular weight-dependent fractions were obtained by eluting the mixed solution with 0.1 M Tris-HCl using gel filtration chromatograph (GE Healthcare: AKTA explorer) and a gel filtration chromatography column (0.25-1 column volume).

(3) The fraction obtained in (2) above was mixed with an anti-25-OH vitamin D antibody-bound particle solution comprising 0.4% (w/v) Na deoxycholate salt in an equal volume (condition in the presence of Na deoxycholate). On the other hand, for the condition in the absence of Na deoxycholate, the fraction was mixed with the anti-25-OH vitamin D antibody-bound particle solution comprising no Na deoxycholate in an equal volume.

(4) The subsequent procedures were carried out in the same manner as in (5) to (12) in Example 1.

Figure 4:
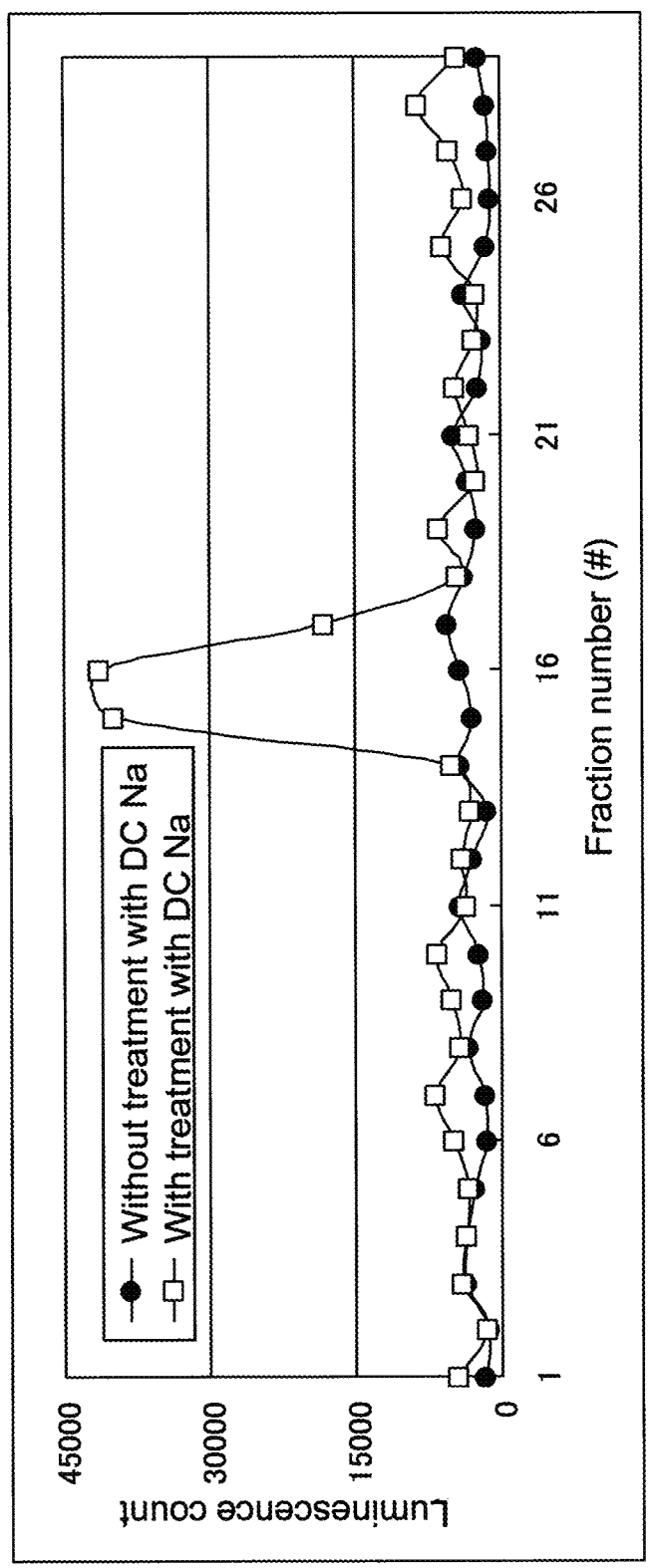
FIG. 4 is a view showing fractions containing 25-OH vitamin D when a human serum sample was eluted with control buffer (Tris-HCl) by gel filtration chromatography. DC Na: sodium deoxycholate (the same applies hereafter)

As a result, when the fraction was not treated with deoxycholate, no significant luminescence count was detected and an amount of 25-OH vitamin D was not able to be measured (FIG. 4). On the other hand, when the fraction was treated with deoxycholate and the amount of 25-OH vitamin D was measured, the strong luminescence count was detected in the fractions #15 to #17.

(8-2) Detection of Vitamin D-Binding Protein in Control Fraction by Western Blotting It was examined whether a fraction of detected vitamin D corresponded to a fraction of vitamin D-binding protein or not.

Specifically, the method was carried out as follows.

(1) To control fraction (fraction obtained in (8-1) above, 30 µL), NuPAGE LSD sample buffer (Invitrogen) in ⅓ times its volume and DTT at a final concentration of 1 mM were added to prepare a mixed solution.

(2) The mixed solution was boiled in an ultrapure water at 100° C. for 5 minutes.

(3) The resulting solution was applied onto a 4 to 10% acrylamide gel.

(4) SDS-PAGE was carried out by applying 200 V of voltage for 25 minutes.

(5) The resulting gel was transferred onto a PVDF membrane utilizing iBlot (Invitrogen).

(6) The membrane on which bands had been transferred was placed into a 5% skim milk solution, and shaken at room temperature for one hour.

(7) The solution was changed to PBSt, and the band-transferred membrane was shaken for 5 minutes for washing.

(8) The above washing procedure was further repeated twice, and subsequently the solution was changed to the 5% skim milk solution.

(9) An anti-human vitamin D-binding protein antibody (Abcam) as a primary antibody at a final concentration of 1 µg/mL was added to the 5% skim milk solution, and the band-transferred membrane was shaken at 4° C. overnight.

(10) The solution was changed to PBSt, the band-transferred membrane was shaken for 5 minutes for washing.

(11) The above procedure was further repeated twice. Subsequently, the solution was changed to the 5% skim milk.

(12) An anti-mouse Ig antibody-HRT as a secondary antibody at 1000 times dilution was added to the 5% skim milk solution, and the membrane was shaken at room temperature for one hour.

(13) The solution was changed to PBSt, and the membrane was shaken for 5 minutes for washing.

(14) The above procedure was further repeated twice. Subsequently, PBSt was changed to ultrapure water.

(15) The band-transferred membrane was rinsed once with the ultrapure water.

(16) The solution was changed to a solution of a luminescence substance (ECL select; GE healthcare).

(17) The band-transferred membrane was photographed using LAS3000 MINWIN (FUJIFILM).

Figure 5:
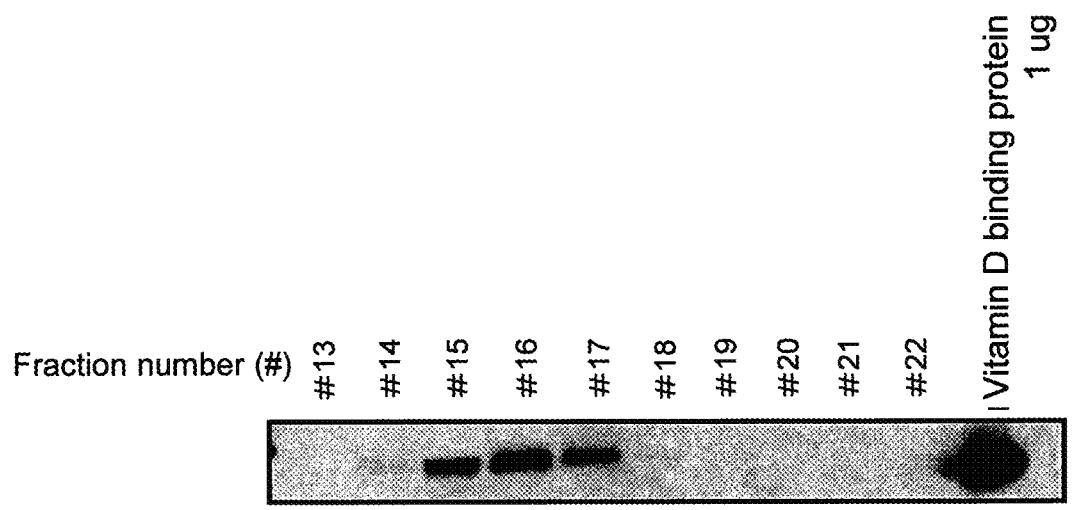
FIG. 5 is a view showing fractions containing a vitamin D-binding protein obtained by western blotting.

As a result, the fractions #15 to #17 in which the vitamin D-binding protein had been detected corresponded to the fractions in which 25-OH vitamin D had been detected in Example 8-1 (FIG. 5). Therefore, when the sample is treated and eluted with 0.1 M Tris-HCl, it has been suggested that the 25-OH vitamin D is recovered in a state of being bound to the vitamin D-binding protein.

(8-3) Dissociation of Vitamin D from Vitamin D-Binding Protein by Surfactant Having Steroid Skeleton It was examined whether 25-OH vitamin D is liberated in human serum by the treatment with deoxycholate or not.

Specifically, the method was carried out as follows.

(1) To human serum or a 1% BSA/PBS solution in which 143 ng/mL of 25-OH vitamin D had been added (50 μL), 0.4% (w/v) deoxycholate solution in 4 times its volume (200 μL) was added to prepare a mixed solution. The mixed solution was prepared by mixing alone with stirring (for about 3 seconds) (i.e., without incubation).

(2) Molecular weight-dependent fractions were obtained by eluting the mixed solution with the 0.4% deoxycholate solution using gel filtration chromatograph (GE Healthcare: AKTA explorer) and a gel filtration chromatography column (Superdex200 10/30). Then 0.25-1 volumes of a column volume were collected.

(3) The sample treated as above was mixed with an anti-25-OH vitamin D antibody-bound magnetic particle solution comprising no deoxycholate in an equal volume.

(4) The subsequent procedures were carried out in the same manner as in (5) to (12) in Example 1.

Figure 6:
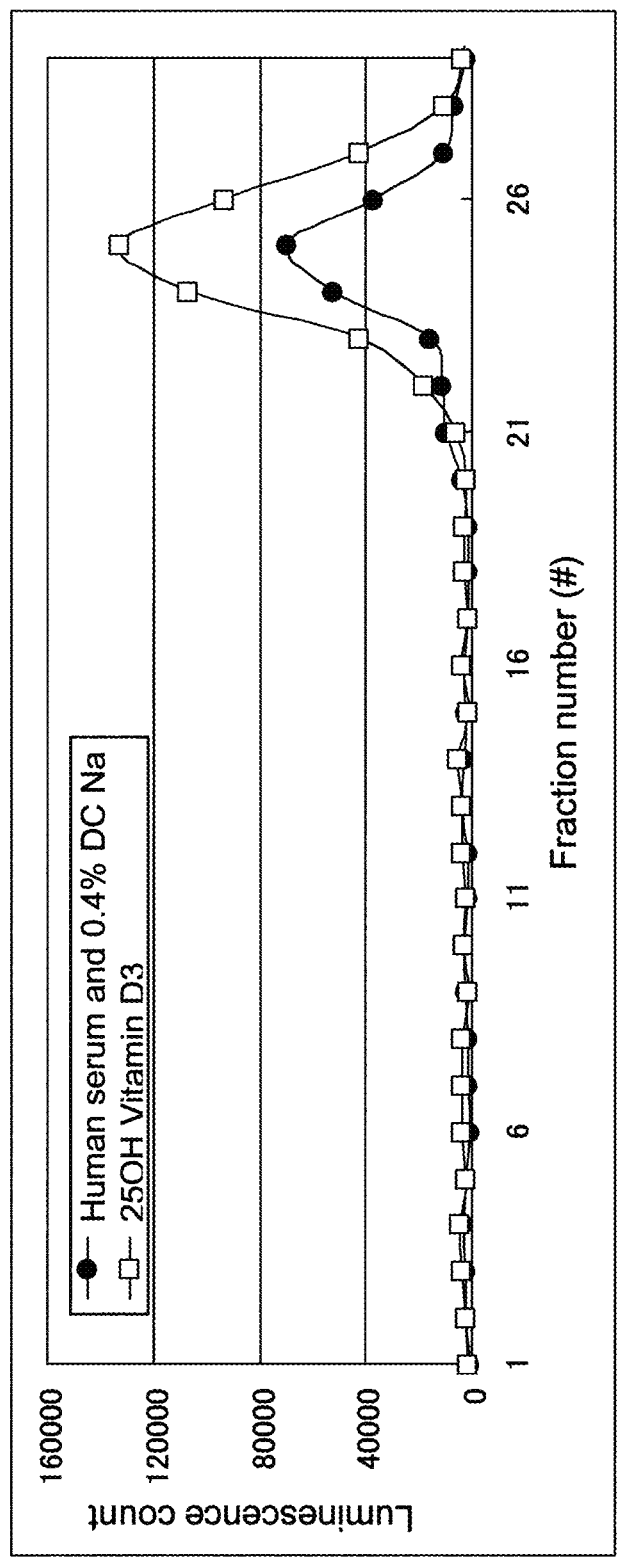
FIG. 6 is a view showing fractions of human serum vitamin D and free vitamin D eluted with a solution of sodium deoxycholate by gel filtration chromatography.

As a result, the 25-OH vitamin D was detected in fractions #22 to #28 that corresponded to smaller molecular weights than those in the fractions #15 to #17 in which the vitamin D-binding protein had been detected in Example 8-1 (FIG. 6). The fractions #22 to #28 in which the 25-OH vitamin D when eluted with deoxycholate was detected is identical to the fractions #22 to #28 in which free 25-OH vitamin D was eluted, suggesting that the 25-OH vitamin D in the human serum is liberated by the treatment with deoxycholate.

(8-4) Release of 25-OH Vitamin D from Vitamin D-Binding Protein and Serum by Treatment with Surfactant Having Steroid Skeleton It was examined whether 25-OH vitamin D is released or not from a complex of the vitamin D-binding protein and 25-OH vitamin D3 by the treatment with the surfactant having the steroid skeleton.

Specifically, the method was carried out as follows.

(1) Samples were prepared as shown in Table 8. Specifically, 2.82 μL of 1 mg/ml 25-OH vitamin D3 (Tronto chemical reagent) (+/−) was added to 17.2 μL of 1.64 mg/ml purified vitamin D-binding protein (Abcam) (+ or −) to prepare the sample. Then, the resulting sample was incubated for 10 minutes.

(2) To 3.75 μL of the above sample, 146.25 μL of a solution shown in Table 8 (pH 7.6, Tris-HCl buffer, 0.138% (w/v) sodium deoxycholate plus 0.038% BSA plus the anti-25-OH vitamin D antibody bound particle solution) to prepare a mixed solution.

(3) The subsequent procedures were carried out in the same manner as in (5) to (12) in Example 1.

TABLE 8

Details of experimental conditions

| | Sample | | |
|---|---|---|---|
| No. | 25-OH vitamin D3 | Vitamin D binding protein | Deoxycholate treatment |
| 1 | + | − | + |
| 2 | + | + | − |
| 3 | + | + | + |
| 4 | − | − | − |

Figure 7:
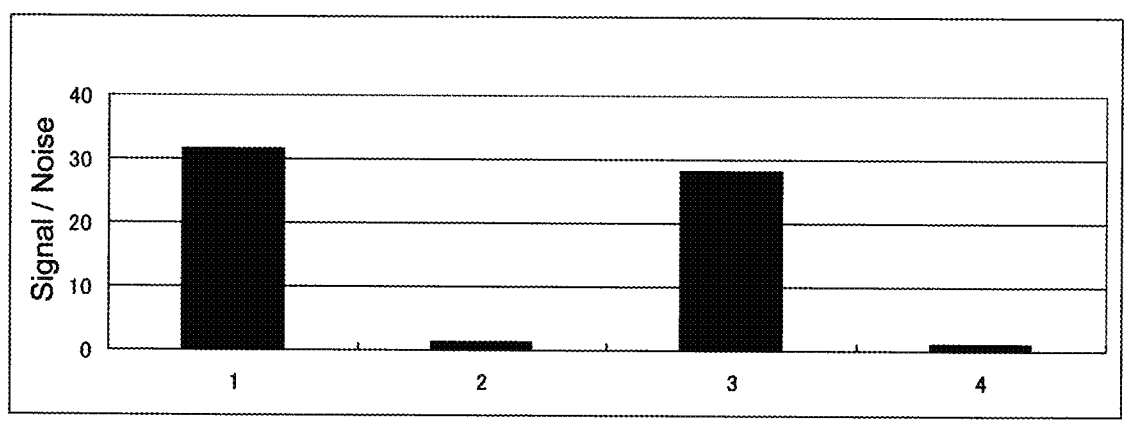
FIG. 7 is a graph illustrating release of 25-OH vitamin D3 from a complex of a vitamin D-binding protein and 25-OH vitamin D3. For experimental conditions for 1 to 4, see Table 8.

As a result, when the complex of the vitamin D-binding protein and 25-OH vitamin D3 was formed using the commercially available vitamin D-binding protein and 25-OH vitamin D3, the 25-OH vitamin D3 was not able to be detected (see FIG. 7 and No. 2 in Table 8). On the other hand, when the complex was treated with deoxycholate, the 25-OH vitamin D3 was able to be detected (see FIG. 7 and No. 3 in Table 8). In this case, the measured count was 88% of the count measured in No. 1 (FIG. 7 and Table 8).

As described above, it has been demonstrated that 25-OH vitamin D is released from the complex of the vitamin D-binding protein and the 25-OH vitamin D and the released 25-OH vitamin D can be measured with high sensitivity by the treatment with the surfactant having the steroid skeleton.

INDUSTRIAL APPLICABILITY

The method and the kit of the present invention are useful for the measurement of vitamin D.

The invention clamed is:

1. A method of measuring a vitamin D in a blood-related sample, comprising:
    (1) treating the blood-related sample comprising a complex of the vitamin D bound to a vitamin D binding protein (DBP) with a surfactant having a steroid skeleton having no hydroxyl group at position 7 in an amount sufficient to release a vitamin D from a complex of the vitamin D and a vitamin D binding protein (DBP), to obtain a treated blood-related sample comprising the vitamin D released from the complex and the surfactant; and
    (2) immunologically detecting a vitamin D in the treated blood-related sample with an antibody against vitamin D,
    wherein the blood-related sample is whole blood, serum or plasma.

2. The method according to claim 1, wherein the surfactant is a bile acid or a derivative thereof or a salt thereof.

3. The method according to claim 1, wherein the surfactant is deoxycholic acid or taurodeoxycholic acid or a salt thereof.

4. The method according to claim 1, further comprising treating the blood-related sample with another denaturating agent that is different from the surfactant.

5. The method according to claim 4, wherein the another denaturating agent is a surfactant comprising a hydrophobic moiety comprising a hydrocarbon chain and a hydrophilic moiety.

6. The method according to claim 1, wherein the treatment of the blood-related sample is carried out by mixing alone.

7. The method according to claim 1, comprising:
    (1') treating the blood-related sample with a reaction solution comprising the surfactant having a steroid skeleton having no hydroxyl group at position 7 and the antibody against vitamin D; and (2') immunologically detecting the vitamin D in the treated blood-related sample.

8. The method according to claim 1, comprising:
(1") treating the blood-related sample with a pretreatment solution comprising a denaturating agent;
(2") treating the blood-related sample treated in (1") above with a diluting solution comprising the surfactant having a steroid skeleton having no hydroxyl group at position 7; and
(3") immunologically detecting the vitamin D in the sample treated in (2") above.

9. The method according to claim 1, wherein the blood-related sample is derived from a human.

10. The method according to claim 1, wherein the treating comprises:
(a) mixing the blood-related sample with an aqueous solution containing the effective concentration of the surfactant for 30 seconds or less to prepare a mixed solution comprising the vitamin D released from the complex and the surfactant; and
(b) incubating the mixed solution for 60 minutes or less.

11. A kit for measuring a vitamin D, comprising:
(1) an effective concentration of a surfactant having a steroid skeleton having no hydroxyl group at position 7 in an aqueous solution which is sufficient to release a vitamin D from a complex of the vitamin D bound to a vitamin D binding protein (DBP);
(2) an antibody against vitamin D and/or a vitamin D standard; and
(3) reagents for an immunological measurement of the antibody.

* * * * *